US012588863B2

(12) United States Patent

Treasure

(10) Patent No.: US 12,588,863 B2

(45) Date of Patent: *Mar. 31, 2026

(54) SYSTEMS AND METHODS FOR PREVENTING AND TREATING WRINKLES

(71) Applicant: Peachy Corp., New York, NY (US)

(72) Inventor: Carolyn Treasure, New York, NY (US)

(73) Assignee: Peachy Corp., New York, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/665,516

(22) Filed: May 15, 2024

(65) Prior Publication Data

US 2024/0306981 A1     Sep. 19, 2024

Related U.S. Application Data

(63) Continuation of application No. 17/323,379, filed on May 18, 2021, now Pat. No. 12,011,284.

(60) Provisional application No. 63/027,033, filed on May 19, 2020.

(51) Int. Cl.
| | |
|---|---|
| *A61B 5/00* | (2006.01) |
| *G06T 7/00* | (2017.01) |
| *G16H 20/17* | (2018.01) |
| *A61K 38/48* | (2006.01) |

(52) U.S. Cl.
CPC ............ *A61B 5/442* (2013.01); *A61B 5/4519* (2013.01); *A61B 5/7264* (2013.01); *G06T 7/0012* (2013.01); *G16H 20/17* (2018.01); *A61K 38/4893* (2013.01); *G06T 2207/20081* (2013.01); *G06T 2207/20084* (2013.01)

(58) Field of Classification Search
CPC ..... A61B 5/442; A61B 5/7264; A61B 5/4519; G16H 20/17; G06T 7/0012; A61K 38/4893; G07T 2207/20081; G07T 2207/20084
See application file for complete search history.

(56) References Cited

U.S. PATENT DOCUMENTS

| | | | | |
|---|---|---|---|---|
| 2013/0197397 | A1* | 8/2013 | Waugh ................. | A61B 5/1072 600/587 |
| 2016/0122820 | A1* | 5/2016 | Zhuang ................. | A61K 8/361 506/17 |
| 2019/0213453 | A1* | 7/2019 | Ludwinski ........... | G06V 40/168 |
| 2023/0346674 | A1* | 11/2023 | Grigore ................. | A61Q 19/08 |

FOREIGN PATENT DOCUMENTS

| | | | | | |
|---|---|---|---|---|---|
| CN | 101098705 | A | * | 1/2008 | .......... A61K 31/454 |
| CN | 105189531 | B | * | 2/2020 | ............. A61P 17/00 |
| EP | 3305370 | A1 | * | 4/2018 | ............... C12N 1/12 |
| JP | 2014040430 | A | * | 3/2014 | .......... C07K 16/249 |

* cited by examiner

*Primary Examiner* — Khai M Nguyen
(74) *Attorney, Agent, or Firm* — Danielson Legal LLC

(57) ABSTRACT

Systems and methods for determining a patient treatment plan to prevent or treat wrinkles using a neural network. The method includes receiving, by a computing device, patient data including at least a dynamic index and a static index for at least one muscle group of a patient. The method also includes determining, by the computing device, based on the patient data, a patient treatment plan including at least one dose of a treating compound to be administered to the patient at one or more application locations on the patient. The method further includes providing, by the computing device, the patient treatment plan for use in preventing or treating wrinkles on the patient.

18 Claims, 9 Drawing Sheets

900

Receive patient data including at least a dynamic index and a static index for at least one muscle group of a patient

902

Determine, based on the patient data, a patient treatment plan including at least one does of a treating compound to be administered to the patient at one or more application locations on the patient

904

Provide the patient treatment plan for use in preventing or treating wrinkles on the patient

906

100

200

200

DATA
COMMUNICATIONS
NETWORK
150

250

250

250

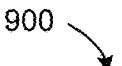

900

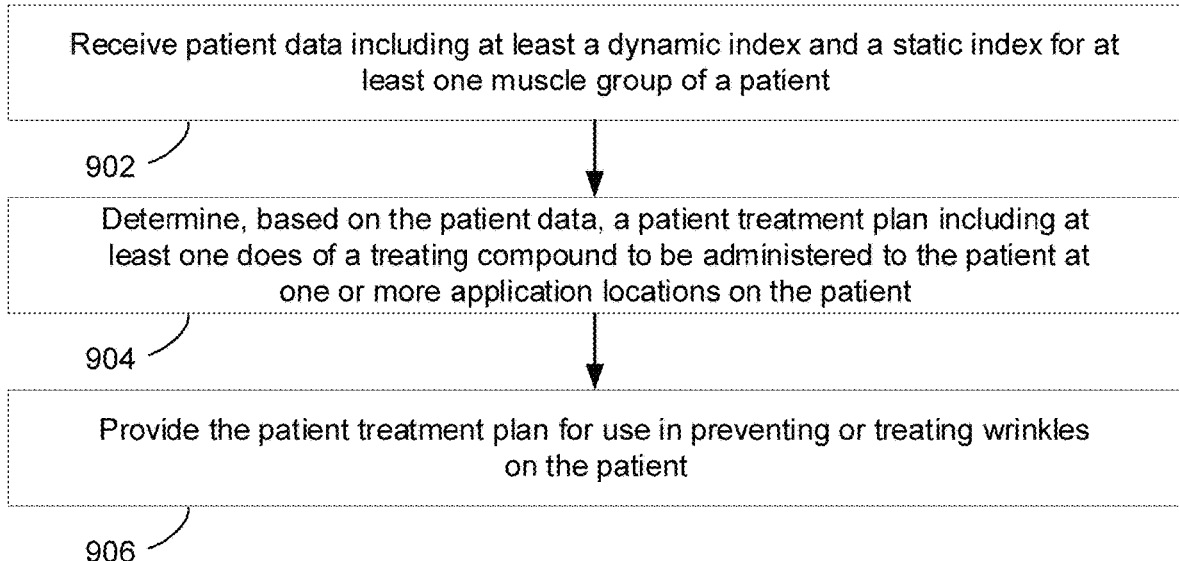

Receive patient data including at least a dynamic index and a static index for at least one muscle group of a patient

902

Determine, based on the patient data, a patient treatment plan including at least one does of a treating compound to be administered to the patient at one or more application locations on the patient

904

Provide the patient treatment plan for use in preventing or treating wrinkles on the patient

SYSTEMS AND METHODS FOR PREVENTING AND TREATING WRINKLES

CROSS REFERENCE TO RELATED APPLICATIONS

This application is a continuation of U.S. application Ser. No. 17/323,379, filed on May 18, 2021, which claims the benefit of and priority to U.S. Provisional Patent Application No. 63/027,033, filed May 19, 2020, the entire disclosure of each of which are owned by the assignee of the instant application and incorporated herein by reference as if set forth in their entirety herein.

FIELD OF THE INVENTION

The present invention relates generally to systems and methods for preventing and treating wrinkles, including systems and methods for determining dosage of a treatment compound.

BACKGROUND OF THE INVENTION

Botulinum toxin serotype A (BoNT-A) is efficacious for preventing facial wrinkles while maintaining natural muscle movement. This preventative use can rely on both the muscle groups targeted and dosing treatment plan. Specifically, BoNT-A can prevent and/or slow the progression of dynamic wrinkles to static wrinkles. Dynamic wrinkles are those that occur when you move the muscles of your face. Static wrinkles are those that are present when your face is at rest. Repeated muscle contractions cause dynamic lines to transition to static lines. BoNT-A is a neuromodulator that inhibits the release of acetylcholine into a neuromuscular junction. With less acetylcholine in the neuromuscular junction, the targeted muscles cannot contract as fervently. This relative relaxation of the targeted muscle prevents the dynamic to static wrinkle transition. There is a dose-dependent relationship between the muscle strength (proxied by amount and depth of dynamic lines) and desired muscle movement after BoNT-A has taken full effect in inhibiting the release of acetylcholine (approximately 2 weeks post-treatment). However, no effort has been made to quantify, predict and implement treatment plans based on this dose-dependent relationship.

SUMMARY OF THE INVENTION

Accordingly, an object of the invention is to provide systems and methods, including computer programs, for preventing and treating wrinkles, e.g., certain systems and methods implementing a novel multivariate algorithm that is used to determine specific doses of a treating compound (e.g., BoNT-A), and/or locations on the patient to apply (e.g., inject) the treating compound, for use in a treatment plan designed to prevent and/or treat facial wrinkles.

In some aspects, a computerized method for determining a patient treatment plan to prevent or treat wrinkles using a neural network includes receiving, by a computing device, patient data including at least a dynamic index and a static index for at least one muscle group of a patient. For example, in some embodiments, the method includes receiving at least one digital image of the patient from a user device. In some embodiments, the method includes determining the dynamic index and the static index for the at least one muscle group of the patient based on at least the digital image. In some embodiments, the dynamic index and the static index for the at least one muscle group of the patient is determined using a machine learning algorithm. In some embodiments, each of the dynamic index and the static index includes a range of whole number values. In some embodiments, the at least one muscle group of the patient includes at least one of glabella muscle group (corrugator supercilii, depressor supercilii, procerus muscles), frontalis muscle, and Orbicularis oculi muscle.

The method also includes determining, by the computing device, based on the patient data, a patient treatment plan including at least one dose of a treating compound to be administered to the patient at one or more application locations on the patient. For example, in some embodiments, the patient treatment plan is determined, based on the patient data, using the neural network. In some embodiments, the treating compound includes BoNT-A.

The method further includes providing, by the computing device, the patient treatment plan for use in preventing or treating wrinkles on the patient. For example, in some embodiments, the method includes generating for display the patient treatment plan on the user device. In some embodiments, the method includes overlaying the patient treatment plan on the at least one digital image of the patient.

In some aspects, a system for determining a patient treatment plan to prevent or treat wrinkles using a neural network includes a computing device communicatively coupled to a user device and a database over a network. The computing device is configured to receive patient data including at least a dynamic index and a static index for at least one muscle group of a patient. For example, in some embodiments, the computing device is further configured to receive at least one digital image of the patient from the user device.

In some embodiments, the computing device is further configured to determine the dynamic index and the static index for the at least one muscle group of the patient based on at least the digital image. In some embodiments, the dynamic index and the static index for the at least one muscle group of the patient is determined using a machine learning algorithm. In some embodiments, each of the dynamic index and the static index includes a range of whole number values. In some embodiments, the at least one muscle group of the patient includes at least one of glabella, frontalis, and Orbicularis oculi.

The computing device is also configured to determine, based on the patient data, a patient treatment plan including at least one dose of a treating compound to be administered to the patient at one or more application locations on the patient. For example, in some embodiments, the patient treatment plan is determined, based on the patient data, using the neural network. In some embodiments, the treating compound includes BoNT-A.

Further, the computing device is configured to provide the patient treatment plan for use in preventing or treating wrinkles on the patient. For example, in some embodiments, the computing device is further configured to generate for display the patient treatment plan on the user device. In some embodiments, the computing device is further configured to overlay the patient treatment plan on the at least one digital image of the patient.

Other aspects and advantages of the invention can become apparent from the following drawings and description, all of which illustrate the principles of the invention, by way of example only.

BRIEF DESCRIPTION OF THE DRAWINGS

The advantages of the invention described above, together with further advantages, may be better understood by referring to the following description taken in conjunction with the accompanying drawings. The drawings are not necessarily to scale, emphasis instead generally being placed upon illustrating the principles of the invention.

FIG. 9 is a flow diagram of a computer-implemented method for determining a patient treatment plan to prevent or treat wrinkles using a neural network, according to embodiments of the technology described herein.

DETAILED DESCRIPTION OF THE INVENTION

The systems and methods described herein can enable implementation of a neural network application for preventing and treating wrinkles. For example, in some aspects, the systems and methods described herein can include one or more mechanisms or methods for determining specific doses of a treating compound (e.g., BoNT-A), and/or locations on the patient to apply (e.g., inject) the treating compound, for use in a treatment plan designed to prevent and/or treat facial wrinkles. The systems and methods can include mechanisms or methods for receiving patient data including at least a dynamic index and a static index for at least one muscle group of a patient. The systems and methods can includes mechanisms or methods for determining, based on patient data, a patient treatment plan including at least one dose of a treating compound to be administered to the patient at one or more application locations on the patient.

Figure 1:
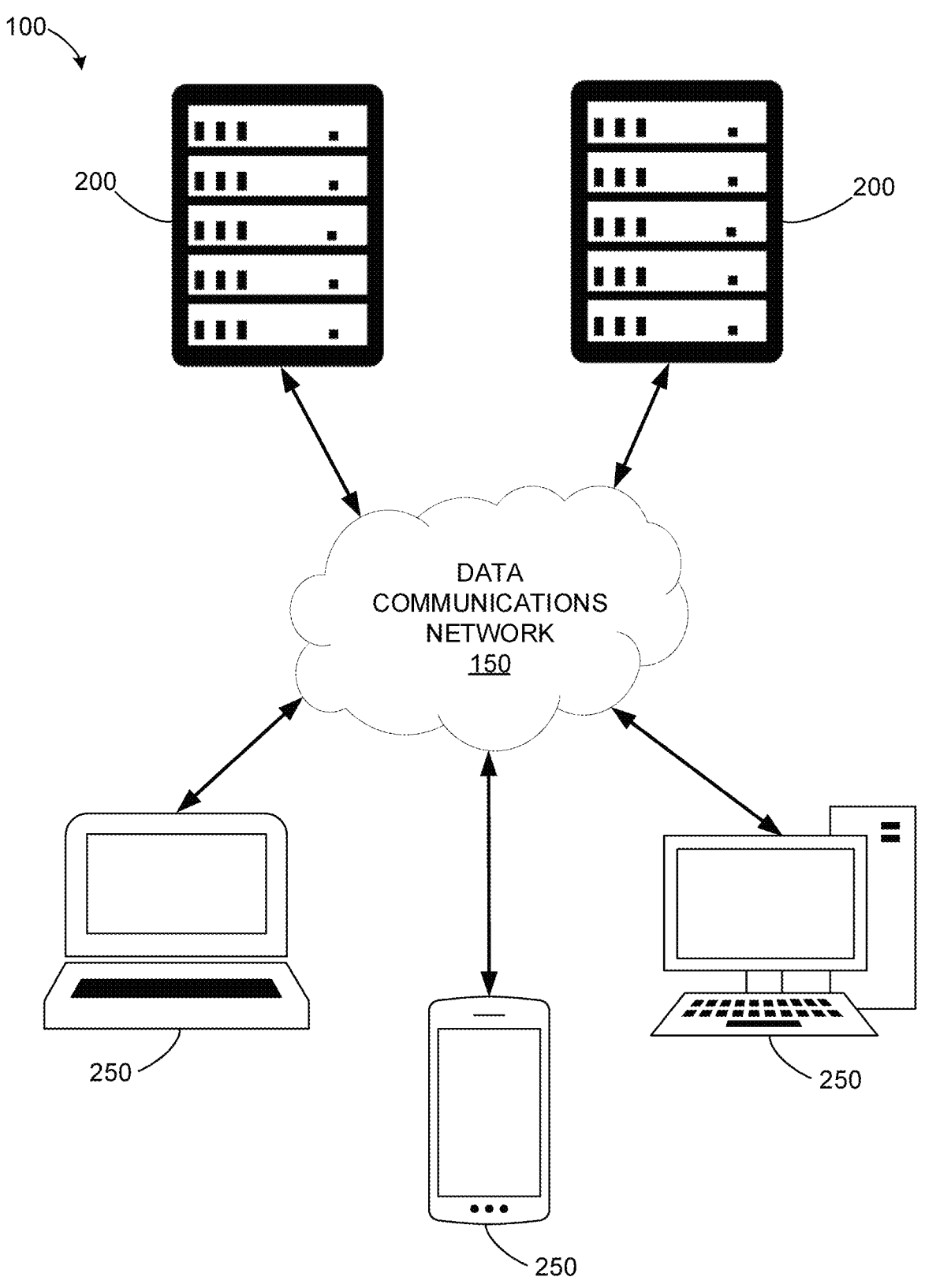
FIG. 1 is a block diagram of an exemplary data communications network, according to embodiments of the technology described herein.
Figure 2:
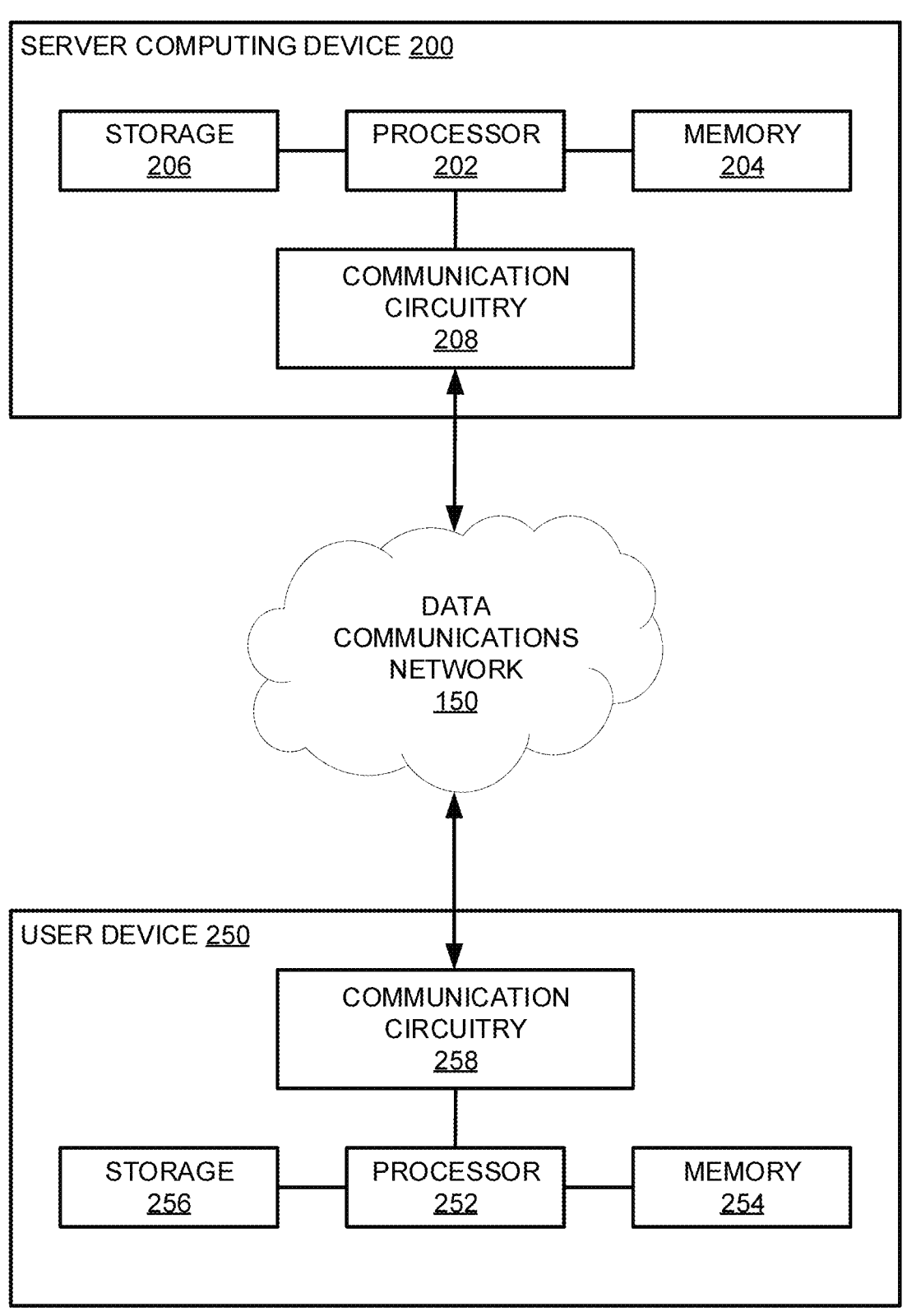
FIG. 2 is a block diagram of an exemplary server computing device and an exemplary user device, according to embodiments of the technology described herein.

The systems and methods described herein can be implemented using a data communications network, server computing devices, and mobile devices. For example, referring to FIGS. 1 and 2, an exemplary communications system 100 includes data communications network 150, exemplary server computing devices 200, and exemplary user devices 250. In some embodiments, the system 100 includes one or more server computing devices 200 and one or more user devices 250. Each server computing device 200 can include a processor 202, memory 204, storage 206, and communication circuitry 208. Each user device 250 can include a processor 252, memory 254, storage 256, and communication circuitry 258. In some embodiments, communication circuitry 208 of the server computing devices 200 is communicatively coupled to the communication circuitry 258 of the user devices 250 via data communications network 150. Communication circuitry 208 and communication circuitry 258 can use Bluetooth, Wi-Fi, or any comparable data transfer connection. The user devices 250 can include personal workstations, laptops, tablets, mobile devices, or any other comparable device.

To quantify the burden of dynamic and static wrinkles, the present technology includes a "Dynamic Index" to quantify a patient's dynamic wrinkle burden for each muscle group where BoNT-A is FDA approved and a "Static Index" to quantify a patient's static wrinkle burden for each muscle group where BoNT-A is FDA approved. Both of these indices can be used as inputs into a dosing algorithm, e.g., for use in a treatment plan. In some embodiments, separate dynamic indices and static indices can be determined for separate muscle groups and can each be used to determine dosing of BoNT-A in a patient's treatment plan.

In some embodiments, the Dynamic Index includes a range of whole number values, e.g., a scale of 1-5. In some embodiments, the following terminology for the glabella muscle group can be used to determine a patient's level on the Dynamic Index: 1) Textural elements: Absence of wrinkles with activity; 2) Dynamic Depressions: Mild depressions in glabellar area surrounded by mild bulging of the glabellar muscles; 3) Dynamic Grooves: Moderate depressions during dynamic activity surrounded by moderate muscle contraction and bulging; 4) Dynamic Furrow: Grooves during dynamic activity surrounded by profound muscle contraction; 5) Deep Dynamic Furrow: Deep grooves during dynamic activity often with significant pull from the lateral corrugators.

In some embodiments, the Static Index also includes a range of whole number values, e.g., a scale of 1-5. In some embodiments, the following terminology for the glabella muscle group can be used to determine a patient's level on the Static Index: 1) No Textural Elements: no relaxed skin tension lines; 2) Faint Textural Elements: relaxed skin tension lines in the glabellar area, typically concentrated at procerus and medial corrugator interdigitation; 3) Fine Wrinkles: Fine linear depressions in the skin surface around the glabellar area; 4) Dermal Crease: Deep linear depression in the skin surface that is deeper and wider than a fine wrinkle. Absence of glabella muscle contraction at rest; 5) Dermal Groove: Deep linear depression with presence of persistent muscle contraction or spasm at rest.

In some embodiments, the Dynamic Index includes a range of whole number values, e.g., a scale of 1-5. In some embodiments, the following terminology for the frontalis muscle can be used to determine a patient's level on the Dynamic Index: 1) Textural elements: Absence of wrinkles with activity—elicited when raising eyebrows; 2) Dynamic Depressions: Mild horizontal depressions in frontalis surrounded by mild bulging of the frontalis muscle; 3) Dynamic Grooves: Moderate horizontal depressions during dynamic activity surrounded by moderate muscle contraction and bulging; 4) Dynamic Furrow: Horizontal grooves during dynamic activity surrounded by profound muscle contraction; 5) Deep Dynamic Furrow: Deep, horizontal grooves during dynamic activity, often with greater than four unique horizontal grooves.

In some embodiments, the Static Index also includes a range of whole number values, e.g., a scale of 1-5. In some embodiments, the following terminology for the frontalis muscle can be used to determine a patient's level on the Static Index: 1) No Textural Elements: no relaxed skin tension lines; 2) Faint Textural Elements: relaxed horizontal skin tension lines in the frontalis, typically concentrated midpoint of the forehead; 3) Fine Wrinkles: Fine horizontal depressions in the skin surface extending up the entirety of the frontalis; 4) Dermal Crease: Deep linear depression in the skin surface that is deeper and wider than a fine wrinkle. Absence of frontalis muscle contraction at rest; 5) Dermal Groove: Deep linear depression with presence of persistent muscle contraction or spasm at rest.

In some embodiments, the Dynamic Index includes a range of whole number values, e.g., a scale of 1-5. In some embodiments, the following terminology for the Orbicularis oculi muscle can be used to determine a patient's level on the Dynamic Index for lateral canthal lines: 1) Textural elements: Absence of wrinkles with activity—elicited most commonly with exaggerated smile; 2) Dynamic Depressions: Mild depressions in Orbicularis oculi extending horizontally from the lateral canthus; 3) Dynamic Grooves: Moderate depressions during dynamic activity surrounded by moderate muscle contraction and bulging; 4) Dynamic Furrow: Fan-shaped grooves during dynamic activity surrounded by profound muscle contraction; 5) Deep Dynamic Furrow: Deep grooves during dynamic activity, often extending in a fan shaped pattern.

In some embodiments, the Static Index also includes a range of whole number values, e.g., a scale of 1-5. In some embodiments, the following terminology for the Orbicularis oculi muscle can be used to determine a patient's level on the Static Index for lateral canthal lines: 1) No Textural Elements: no relaxed skin tension lines; 2) Faint Textural Elements: relaxed skin tension lines, extending from the lateral canthus; 3) Fine Wrinkles: Fine depressions typically concentrating in a fan-shaped pattern extending from the lateral canthus; 4) Dermal Crease: Deep linear depression in the skin surface that is deeper and wider than a fine wrinkle. Absence of Orbicularis oculi muscle contraction at rest; 5) Dermal Groove: Deep depression with presence of persistent muscle contraction or spasm at rest. Grooves common in either a fan-shaped pattern, inferior-predominant pattern or superior-predominant pattern.

Furthermore, as a part of the intake process, desired amount of muscle movement post-treatment can be discussed with each patient. Exemplary potential responses can be outlined on a Retained Muscle Movement Scale such as the following: 1) Ample amount of muscle movement retained post treatment; 2) Slightly decreased muscle movement from pre-BoNT-A baseline; 3) Natural muscle movement—the recommendation; 4) Limited muscle movement—minimal dynamic lines; 5) Minimal retained muscle movement—no dynamic lines.

Previous research has included other formulations that quantify the amount and intensity of the dynamic and static wrinkles for the face as a whole. The present scales are improved in that they are expanded to each of the FDA approved muscle groups: glabella muscle complex, frontalis muscle, and orbicularis oculi muscle. Each Dynamic and Static Index has specific criteria for each level which is quantified for each patient and used to devise treatment plans. Furthermore, each patient can be asked to quantify the amount of retained muscle movement they prefer post-treatment, with the baseline recommendation being natural amount of muscle movement. In some embodiments, BoNT-A is administered with an emphasis on wrinkle prevention, targeting dynamic wrinkles before they transition to static wrinkles. The emphasis on retaining a significant and natural amount of muscle movement is unique in the industry. The general scale for the Indices allows for standardizing the methodology to scale.

The technology described herein is unique in that it was created with the specific goal of preventing wrinkles while maintaining natural muscle movement. In some embodiments, inputs including Dynamic Indices, gender, desired muscle movement, anatomic variants specific to each muscle group and previous BoNT-A use can be used in a novel algorithm. Specific to each muscle group, there are anatomic variants that effect the proposed treatment plan. For example, for the glabella muscle group, if the patient has dermatochalasis (excess or redundant skin on upper eyes, or colloquially known as "hooding"), it can greatly affect the treatment plan. Additionally, another anatomic variant that is common is eyebrow positioning at or below the orbital rim. Resting eyebrow positioning relative to the orbital rim is a variable that similarly affects the recommended treatment plan. These two anatomic variants are identified with patients and factored into the treatment plan for the glabella muscle group.

For the frontalis muscle, the presence of dermatochalasis can greatly affect the recommend treatment plan, both dose of the specific treatment points and the anatomic placement of the treatment points. Dermatochalasis is identified with patients and used as input variable for the treatment plan of this muscle group. For the lateral canthal lines, the anatomic positioning of the lateral ⅓ ("tail") of the eyebrow is observed. If the positioning falls outside the recommended plane, then a lift can be recommended. This positioning factors into the recommended treatment plan.

Figure 3:
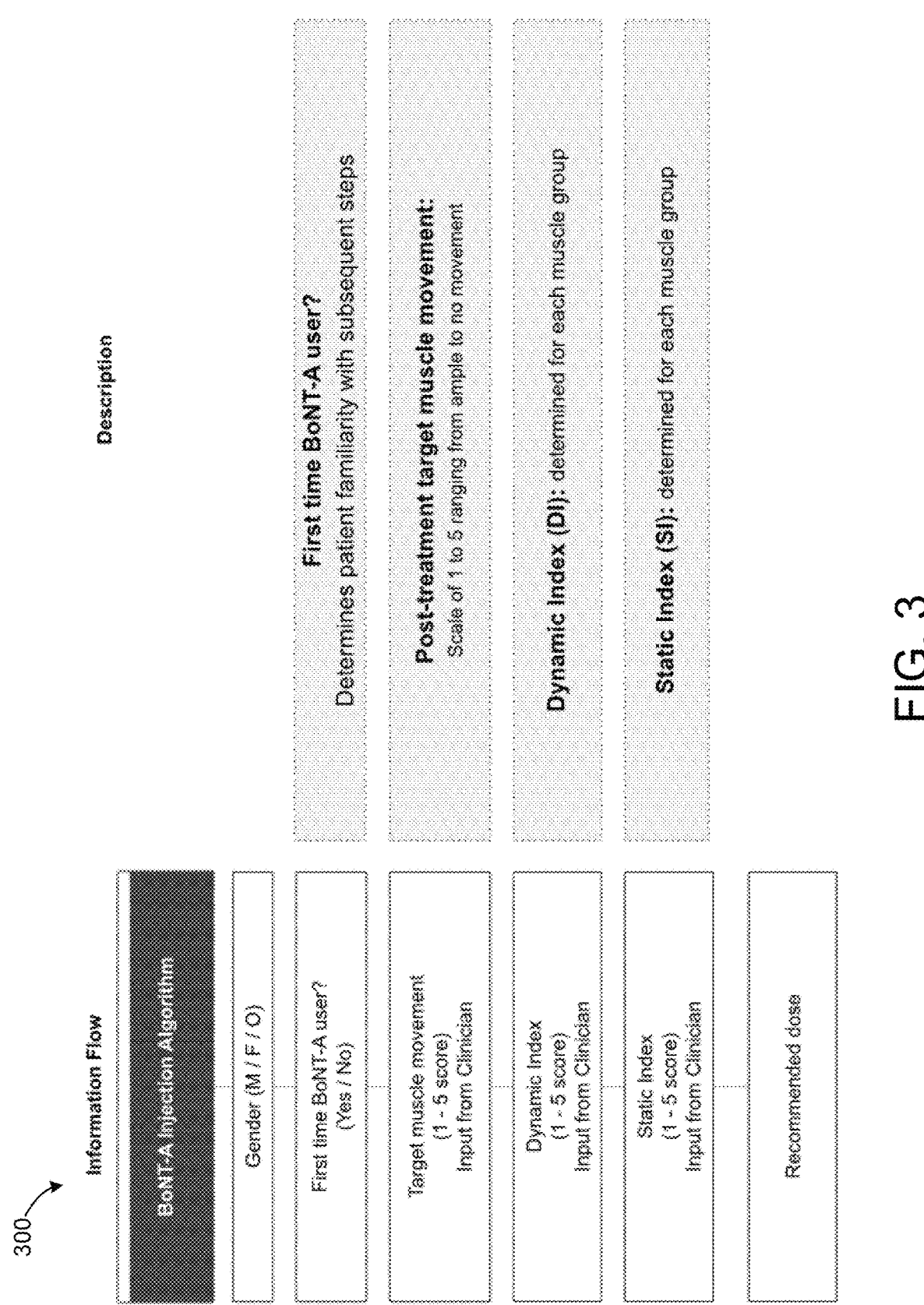
FIG. 3 is a diagram showing an exemplary information flow for a dosing algorithm for each muscle group, according to embodiments of the technology described herein.
Figure 4:
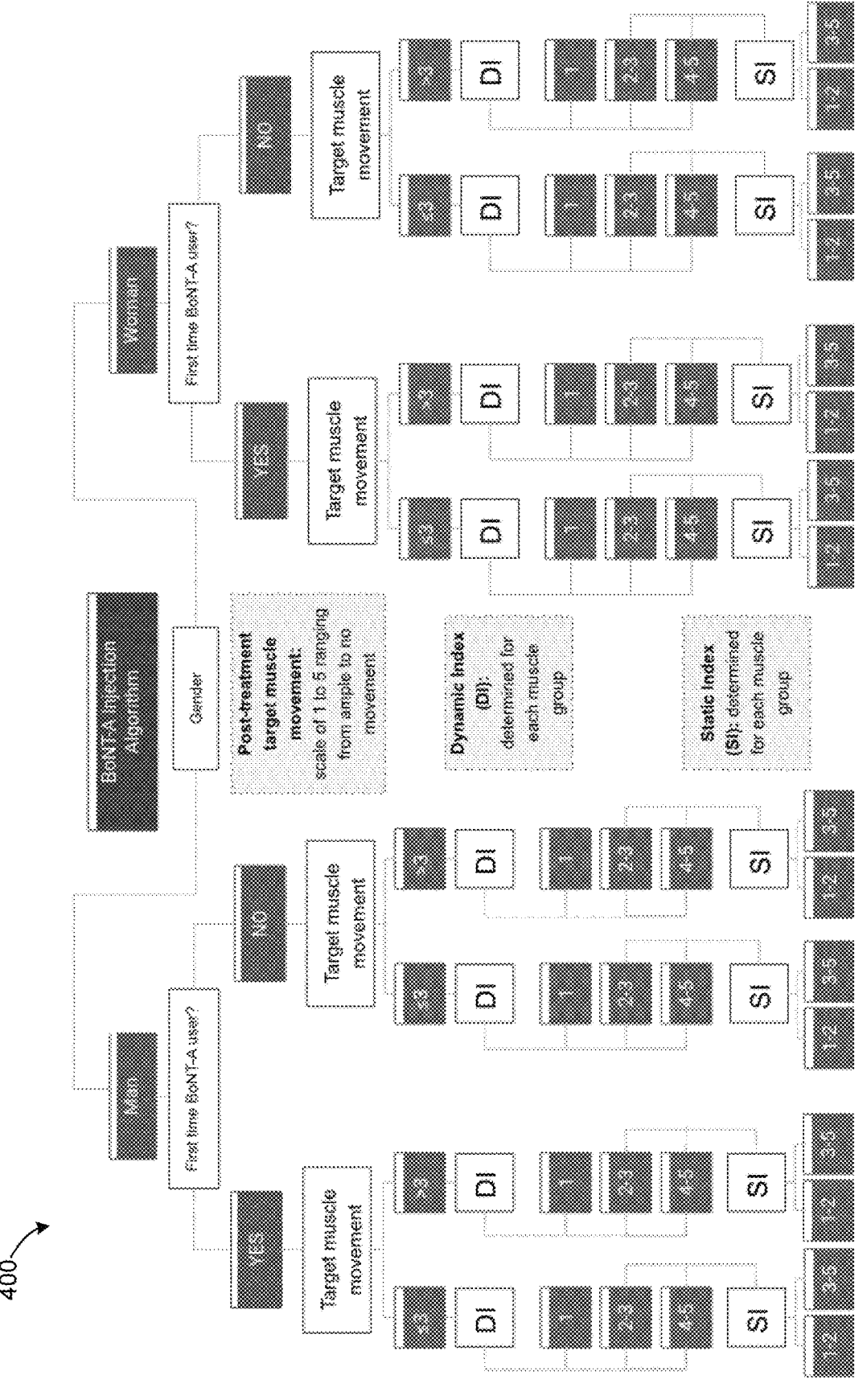
FIG. 4 is a diagram showing an exemplary information flow for a dosing algorithm specific for each muscle group, according to embodiments of the technology described herein.

In one exemplary implementation, de-identified patient data from the clinic was collected. From this data, a standardized, predictive algorithm was created specifying what a provider should prescribe and administer based on the independent variables detailed in FIGS. 3 and 4. The outcome variables are the number of units of BoNT-A for each injection site in the three muscle groups unique to each patient based on the input variables.

Figure 5:
FIG. 5 is a diagram showing an exemplary visualization of a digital image with dynamic index and static index calculations for the glabella muscle group, according to embodiments of the technology described herein.
Figure 6:
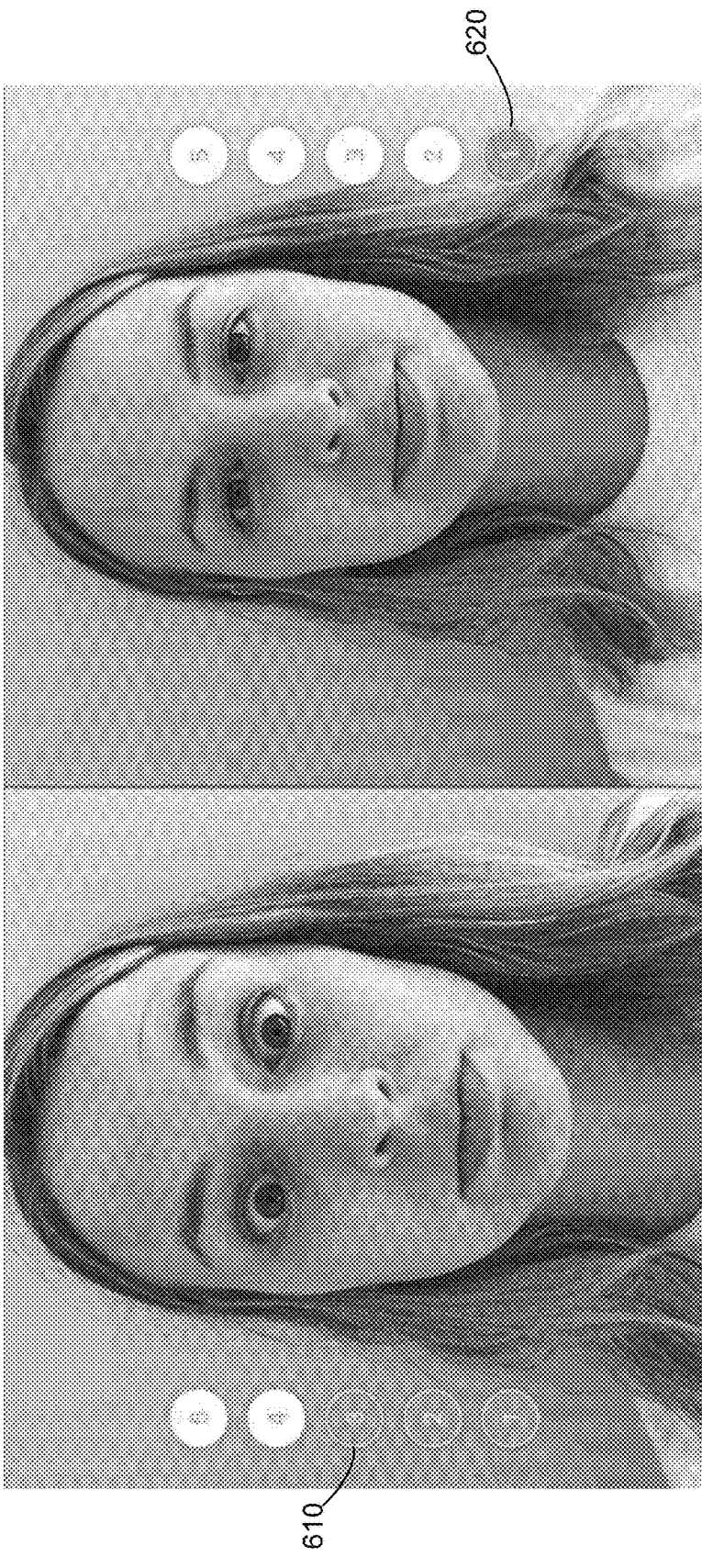
FIG. 6 is a diagram showing an exemplary visualization of a digital image with dynamic index and static index calculations for the frontalis muscle, according to embodiments of the technology described herein.
Figure 7:
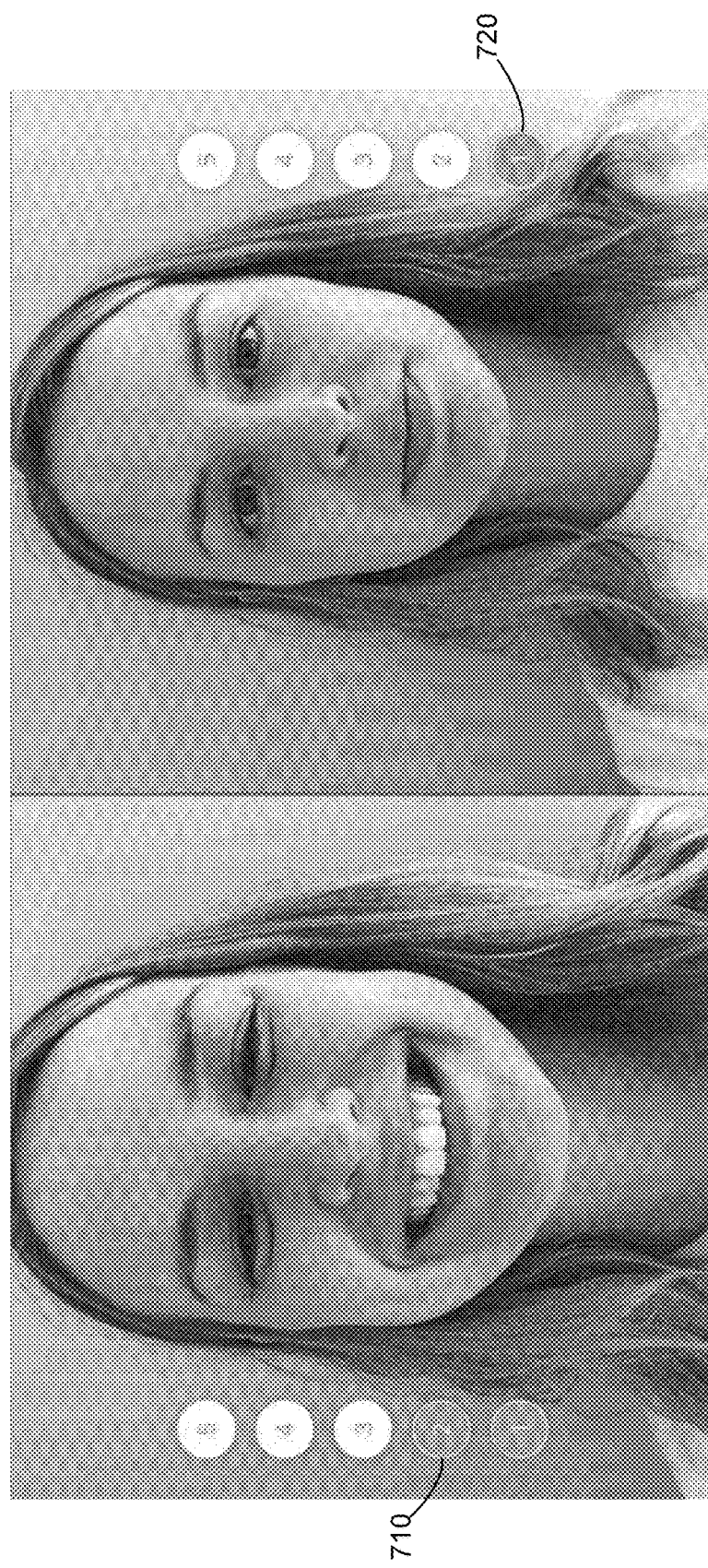
FIG. 7 is a diagram showing an exemplary visualization of a digital image with dynamic index and static index calculations for the Orbicularis oculi muscle, according to embodiments of the technology described herein.

In some embodiments, digital imaging of a human (e.g., a patient's) face can be used for machine learning applications to interpret dynamic and/or static wrinkle burden on epidermal, dermal, subcutaneous, and muscle level and recommended unique treatment plan. For example, in some embodiments, patients are instructed to take a series of facial images (e.g., four images) that help providers evaluate and determine their unique Dynamic Index and Static Index. Each image can be highly standardized to highlight dynamic activity for each FDA-approved site for BoNT-A injections: for example, furrowed eyebrows (glabella muscle complex), elevated eyebrows (frontalis muscle), exaggerated smile (orbicularis oculi muscle which causes lateral canthal lines). FIGS. 5-7 illustrate the Dynamic and Static Index of an exemplary patient.

Referring to FIG. 5, an exemplary dynamic index 510 and static index 520 is illustrated for the Glabella muscle group. The Dynamic Index 510 with active muscle movement is on the left side of the image. The Static Index 520 with relaxed face is located on the right side of the image. Furrowed eyebrows highlight the glabella muscle complex. The Dynamic Index 510 is on a scale of 1 to 5, and the high number with a shaded background highlights the place on the Dynamic Index 510 (in this case 3/5). Similarly, the Static Index 520 is on a scale of 1 to 5 with the number having a shaded background signifying the number on the Static Index 520 (in this case 1/5).

Referring to FIG. 6, an exemplary dynamic index 610 and static index 620 is illustrated for the Frontalis muscle. The Dynamic Index 610 with active muscle movement is on the left side of the image. The Static Index 620 with relaxed face is located on the right side of the image. Elevated eyebrows highlights the frontalis muscle. The Dynamic Index 610 for the Frontalis is on a scale of 1 to 5, and the high number with a shaded background highlights the place on the Dynamic Index 610 (in this case 3/5). Similarly, the Static Index 620 is on a scale of 1 to 5 with the number having a shaded background signifying the number on the Static Index (in this case 1/5).

Referring to FIG. 7, an exemplary dynamic index 710 and static index 720 is illustrated for the Orbicularis Oculi muscle. The Dynamic Index 710 with active muscle movement is on the left side of the image. The Static Index 720 with relaxed face is located on the right side of the image. Exaggerated smile highlight the orbicularis oculi muscle. The Dynamic Index 710 for the Orbicularis oculi is on a scale of 1 to 5, and the high number having a shaded background highlights the place on the Dynamic Index 710 (in this case 2/5). Similarly, the Static Index 720 is on a scale of 1 to 5 with the number having a shaded background signifying the number on the Static Index 720 (in this case 1/5).

The techniques described herein can be implemented using supervised learning and/or machine learning algorithms. Supervised learning is the machine learning task of learning a function that maps an input to an output based on example input-output pairs. It infers a function from labeled training data consisting of a set of training examples. Each example is a pair consisting of an input object and a desired output value. A supervised learning algorithm or machine learning algorithm analyzes the training data and produces an inferred function, which can be used for mapping new examples.

For example, in some embodiments, additional variables can also be used to develop a tailored treatment plan for each of one or more (e.g., three) muscle groups in each patient. Multivariate regression analysis can be performed for each of three muscle groups using de-identified patient data for each of the independent variables outlined below. From the multivariate regression analysis, an exemplary predictive algorithm can be developed and used to calculate recommended total dosages for each of the three muscle groups based on facial muscle anatomy and preference. In some embodiments, the algorithm can be further refined using feedback from patients.

Figure 8:
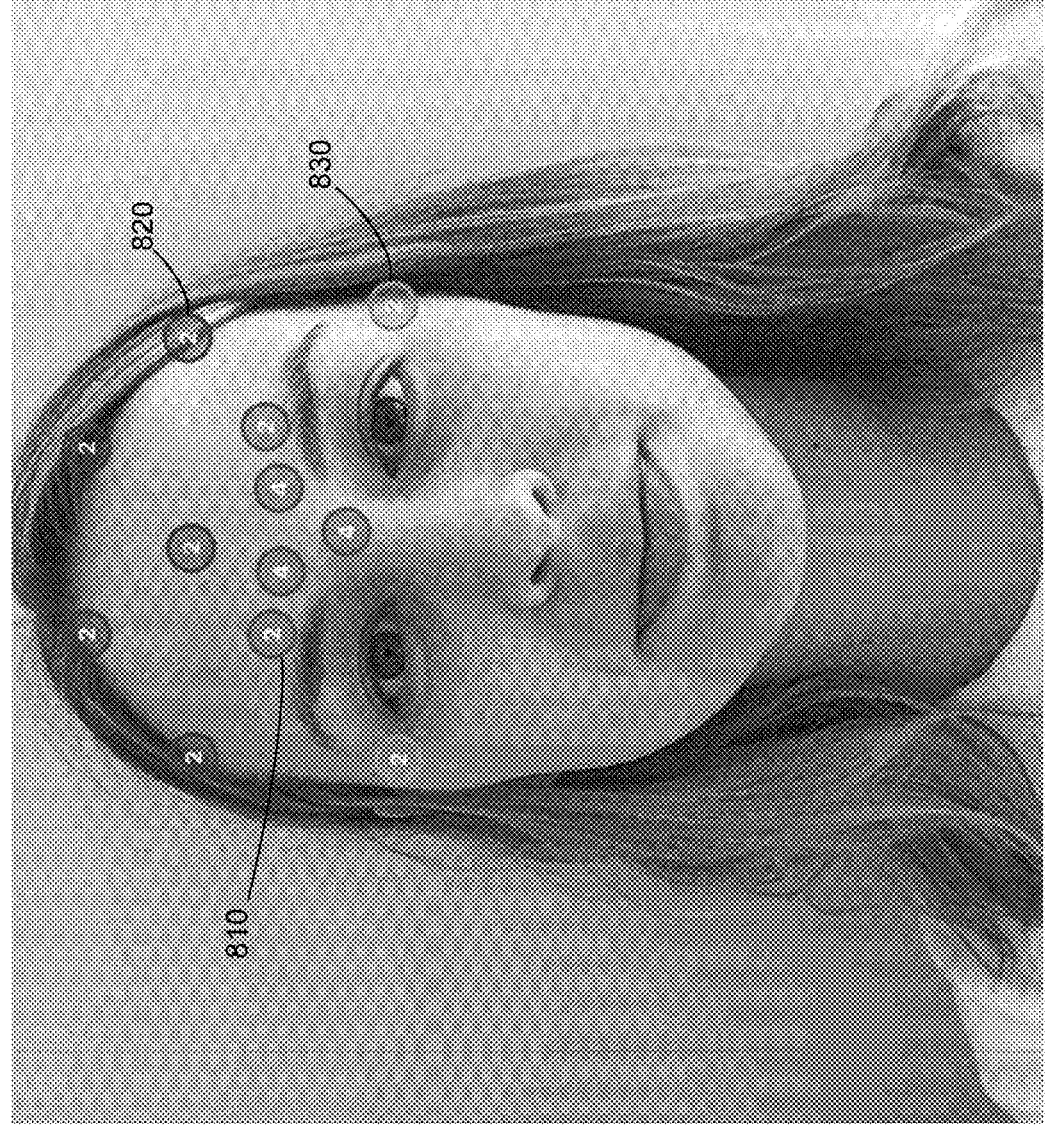
FIG. 8 is a diagram showing a visualization of an exemplary treatment plan overlaid on a digital image of a patient, according to embodiments of the technology described herein.

Referring to FIG. 8, an exemplary treatment plan overlaid on a digital image of a patient is illustrated. The placement of the circles indicates the specific injection points. In some embodiments, colors highlight each of the separate muscle groups. For example, gray can denote the injection points 810 corresponding to Glabellar complex; blue can denote the injection points 820 corresponding to the Frontalis muscle; and green can denote the injection points 830 corresponding to the Orbicularis oculi. The numbers inside the circles are the specific amount of units that the algorithm determines for the patient.

Using patient data (n=286), three separate ordinary least squares analyses were performed for each of the three muscle groups using the 5 variables for each regression (gender, previous BoNT-A user, targeted muscle movement, Dynamic Index and Static Index). Each of these regressions demonstrated a strong correlation ($R^2$=0.87-0.92) with the dependent variable of total dose of BoNT-A for each muscle group.

Follow-up analyses and studies have been conducted with additional patient data (n=3059). Separate ordinary least squares analyses were performed for each of the three muscle groups using the variables listed below for each regression. Each of these regressions demonstrated a strong correlation ($R^2$=0.89-0.94) with the dependent variable of the total dose and placement of BoNT-A for each of the three muscle groups.

In some embodiments, the following independent variables can be used in the treatment plan algorithm and placement recommendation: Gender (self-identified); First time BoNT-A user (binary—yes, no); Post-treatment target muscle movement (scale of 1 to 5 ranging from ample to no retained muscle movement); Anatomic variants: resting eyebrow positioning, dermatochalasis, and eyebrow tail positioning; Dynamic Index—determined for each muscle group; Static Index-determined for each muscle group.

The unique patterns and strength of both dynamic and static activity in addition to anatomic variants discussed previously effect the placement of the treatment points in addition to specific dose. This developed process takes these into account as well when recommending placement of the specific treatment points in each of the muscle groups.

Referring to FIG. 9, a process 900 for determining a patient treatment plan to prevent or treat wrinkles using a neural network is illustrated. The process 900 begins by receiving, by a computing device 200, patient data including at least a dynamic index and a static index for at least one muscle group of a patient in step 902. For example, in some embodiments, the process 900 includes receiving at least one digital image of the patient from a user device 250. In some embodiments, process 900 includes determining the dynamic index and the static index for the at least one muscle group of the patient based on at least the digital image. In some embodiments, the dynamic index and the static index for the at least one muscle group of the patient is determined using a machine learning algorithm. In some embodiments, each of the dynamic index and the static index includes a range of whole number values. In some embodiments, the at least one muscle group of the patient includes at least one of glabella, frontalis, and Orbicularis oculi.

Process 900 continues by determining, by the computing device 200, based on the patient data, a patient treatment plan including at least one does of a treating compound to be administered to the patient at one or more application locations on the patient in step 904. For example, in some embodiments, the patient treatment plan is determined, based on the patient data, using the neural network. In some embodiments, the treating compound includes BoNT-A.

Process 900 finishes by providing, by the computing device 200, the patient treatment plan for use in preventing or treating wrinkles on the patient in step 906. In some embodiments, the server computing device 200 is configured to store the data file 350 in a database 450. For example, in some embodiments, process 900 includes generating for display the patient treatment plan on the user device. In some embodiments, process 900 includes overlaying the patient treatment plan on the at least one digital image of the patient.

In some aspects, process 900 can be implemented on a system for determining a patient treatment plan to prevent or treat wrinkles using a neural network. The system includes a computing device 200 communicatively coupled to a user device 250 and a database 450 over a network 150. The computing device 200 is configured to receive patient data including at least a dynamic index and a static index for at least one muscle group of a patient. For example, in some embodiments, the computing device 200 is further config-ured to receive at least one digital image of the patient from the user device 250.

In some embodiments, the computing device 200 is further configured to determine the dynamic index and the static index for the at least one muscle group of the patient based on at least the digital image. In some embodiments, the dynamic index and the static index for the at least one muscle group of the patient is determined using a machine learning algorithm. In some embodiments, each of the dynamic index and the static index includes a range of whole number values. In some embodiments, the at least one muscle group of the patient includes at least one of glabella, frontalis, and Orbicularis oculi.

The computing device 200 is also configured to deter-mine, based on the patient data, a patient treatment plan including at least one dose of a treating compound to be administered to the patient at one or more application locations on the patient. For example, in some embodiments, the patient treatment plan is determined, based on the patient data, using the neural network. In some embodiments, the treating compound includes BoNT-A.

Further, the computing device 200 is configured to pro-vide the patient treatment plan for use in preventing or treating wrinkles on the patient. For example, in some embodiments, the computing device 200 is further config-ured to generate for display the patient treatment plan on the user device 250. In some embodiments, the computing device 200 is further configured to overlay the patient treatment plan on the at least one digital image of the patient.

The above-described techniques can be implemented in digital and/or analog electronic circuitry, or in computer hardware, firmware, software, or in combinations of them. The implementation can be as a computer program product, i.e., a computer program tangibly embodied in a machine-readable storage device, for execution by, or to control the operation of, a data processing apparatus, e.g., a program-mable processor, a computer, and/or multiple computers. A computer program can be written in any form of computer or programming language, including source code, compiled code, interpreted code and/or machine code, and the com-puter program can be deployed in any form, including as a stand-alone program or as a subroutine, element, or other unit suitable for use in a computing environment. A com-puter program can be deployed to be executed on one computer or on multiple computers at one or more sites. The computer program can be deployed in a cloud computing environment (e.g., Amazon® AWS, Microsoft® Azure, IBM®).

Method steps can be performed by one or more processors executing a computer program to perform functions of the invention by operating on input data and/or generating output data. Method steps can also be performed by, and an apparatus can be implemented as, special purpose logic circuitry, e.g., a FPGA (field programmable gate array), a FPAA (field-programmable analog array), a CPLD (complex programmable logic device), a PSoC (Programmable Sys-tem-on-Chip), ASIP (application-specific instruction-set processor), or an ASIC (application-specific integrated cir-cuit), or the like. Subroutines can refer to portions of the stored computer program and/or the processor, and/or the special circuitry that implement one or more functions.

Processors suitable for the execution of a computer pro-gram include, by way of example, special purpose micro-processors specifically programmed with instructions executable to perform the methods described herein, and any one or more processors of any kind of digital or analog computer. Generally, a processor receives instructions and data from a read-only memory or a random access memory or both. The essential elements of a computer are a processor for executing instructions and one or more memory devices for storing instructions and/or data. Memory devices, such as a cache, can be used to temporarily store data. Memory devices can also be used for long-term data storage. Gen-erally, a computer also includes, or is operatively coupled to receive data from or transfer data to, or both, one or more mass storage devices for storing data, e.g., magnetic, mag-neto-optical disks, or optical disks. A computer can also be operatively coupled to a communications network in order to receive instructions and/or data from the network and/or to transfer instructions and/or data to the network. Com-puter-readable storage mediums suitable for embodying computer program instructions and data include all forms of volatile and non-volatile memory, including by way of example semiconductor memory devices, e.g., DRAM, SRAM, EPROM, EEPROM, and flash memory devices; magnetic disks, e.g., internal hard disks or removable disks; magneto-optical disks; and optical disks, e.g., CD, DVD, HD-DVD, and Blu-ray disks. The processor and the memory can be supplemented by and/or incorporated in special purpose logic circuitry.

To provide for interaction with a user, the above described techniques can be implemented on a computing device in communication with a display device, e.g., a CRT (cathode ray tube), plasma, or LCD (liquid crystal display) monitor, a mobile device display or screen, a holographic device and/or projector, for displaying information to the user and a keyboard and a pointing device, e.g., a mouse, a trackball, a touchpad, or a motion sensor, by which the user can provide input to the computer (e.g., interact with a user interface element). Other kinds of devices can be used to provide for interaction with a user as well; for example, feedback provided to the user can be any form of sensory feedback, e.g., visual feedback, auditory feedback, or tactile feedback; and input from the user can be received in any form, including acoustic, speech, and/or tactile input.

The above-described techniques can be implemented in a distributed computing system that includes a back-end com-ponent. The back-end component can, for example, be a data server, a middleware component, and/or an application server. The above described techniques can be implemented in a distributed computing system that includes a front-end component. The front-end component can, for example, be a client computer having a graphical user interface, a Web browser through which a user can interact with an example implementation, and/or other graphical user interfaces for a transmitting device. The above described techniques can be implemented in a distributed computing system that includes any combination of such back-end, middleware, or front-end components.

The components of the computing system can be inter-connected by transmission medium, which can include any form or medium of digital or analog data communication (e.g., a communication network). Transmission medium can include one or more packet-based networks and/or one or more circuit-based networks in any configuration. Packet-based networks can include, for example, the Internet, a carrier internet protocol (IP) network (e.g., local area net-work (LAN), wide area network (WAN), campus area network (CAN), metropolitan area network (MAN), home area network (HAN)), a private IP network, an IP private branch exchange (IPBX), a wireless network (e.g., radio access network (RAN), Bluetooth, near field communica-tions (NFC) network, Wi-Fi, WiMAX, general packet radio service (GPRS) network, HiperLAN), and/or other packet-based networks. Circuit-based networks can include, for example, the public switched telephone network (PSTN), a legacy private branch exchange (PBX), a wireless network (e.g., RAN, code-division multiple access (CDMA) network, time division multiple access (TDMA) network, global system for mobile communications (GSM) network), and/or other circuit-based networks.

Information transfer over transmission medium can be based on one or more communication protocols. Communication protocols can include, for example, Ethernet protocol, Internet Protocol (IP), Voice over IP (VOIP), a Peer-to-Peer (P2P) protocol, Hypertext Transfer Protocol (HTTP), Session Initiation Protocol (SIP), H.323, Media Gateway Control Protocol (MGCP), Signaling System #7 (SS7), a Global System for Mobile Communications (GSM) protocol, a Push-to-Talk (PTT) protocol, a PTT over Cellular (POC) protocol, Universal Mobile Telecommunications System (UMTS), 3GPP Long Term Evolution (LTE) and/or other communication protocols.

Devices of the computing system can include, for example, a computer, a computer with a browser device, a telephone, an IP phone, a mobile device (e.g., cellular phone, personal digital assistant (PDA) device, smart phone, tablet, laptop computer, electronic mail device), and/or other communication devices. The browser device includes, for example, a computer (e.g., desktop computer and/or laptop computer) with a World Wide Web browser (e.g., Chrome™ from Google, Inc., Microsoft® Internet Explorer® available from Microsoft Corporation, and/or Mozilla® Firefox available from Mozilla Corporation). Mobile computing device include, for example, a Blackberry® from Research in Motion, an iPhone® from Apple Corporation, and/or an Android™-based device. IP phones include, for example, a Cisco® Unified IP Phone 7985G and/or a Cisco® Unified Wireless Phone 7920 available from Cisco Systems, Inc.

Comprise, include, and/or plural forms of each are open ended and include the listed parts and can include additional parts that are not listed. And/or is open ended and includes one or more of the listed parts and combinations of the listed parts.

One skilled in the art will realize the subject matter may be embodied in other specific forms without departing from the spirit or essential characteristics thereof. The foregoing embodiments are therefore to be considered in all respects illustrative rather than limiting of the subject matter described herein.

What is claimed:

1. A computerized method for determining a patient treatment plan to prevent or treat wrinkles, the computerized method comprising:
   receiving, by a first computing device, patient data including a dynamic index and a static index for at least one muscle group of a patient;
   generating, using the first computing device, a patient treatment plan including at least one dose of botulinum toxin serotype (BoNT-A) to be administered to the patient at one or more application locations on the patient, wherein the patient treatment plan is based on the patient data;
   communicating the patient treatment plan to a database in operable connectivity with the first computing device over a network; and
   obtaining, by a second computing device in operable connectivity with the database over the network, the patient treatment plan, wherein the first computing device and the second computing device are different hardware devices.

2. The computerized method of claim 1 wherein each of the dynamic index and the static index comprises a range of values.

3. The computerized method of claim 1 wherein the range of values of each of the dynamic index and the static index comprises a range of whole number values.

4. The computerized method of claim 1 wherein the first computing device is accessible by a first user and the second computing device is accessible by a second user.

5. The computerized method of claim 4 further comprising:
   receiving an update to the patient treatment plan from the first user,
   storing the update in the database, and
   communicating the updated patient treatment plan to the second computing device.

6. The computerized method of claim 1 wherein the at least one muscle group of the patient comprises at least one of glabella, frontalis, and Orbicularis oculi.

7. The computerized method of claim 1 wherein the dynamic index and the static index for the at least one muscle group of the patient is determined using a machine learning algorithm.

8. The computerized method of claim 1 wherein the first computing device and the second computing device are the same device.

9. The computerized method of claim 1 further comprising overlaying the patient treatment plan on a digital image of the patient.

10. A system for determining a patient treatment plan to prevent or treat wrinkles, the system comprising:
   a first computing device configured to:
      receive patient data including a dynamic index and a static index for at least one muscle group of a patient, and
      generate a patient treatment plan including at least one dose of botulinum toxin serotype (BoNT-A) to be administered to the patient at one or more application locations on the patient, wherein the patient treatment plan is based on the patient data;
   a database in operable connectivity with the first computing device over a network; and
   a second computing device configured to obtain the patient treatment plan from the database, wherein the first computing device and the second computing device are different hardware devices.

11. The system of claim 10 herein each of the dynamic index and the static index comprises a range of values.

12. The system of claim 11 wherein the range of values of each of the dynamic index and the static index comprises a range of whole number values.

13. The system of claim 10 wherein the first computing device is accessible by a first user and the second computing device is accessible by a second user.

14. The system of claim 13 wherein the first computing device is further configured to receive an update to the patient plan from the first user and store the update in the database, wherein the second computing device is further configured to receive the updated patient treatment plan.

15. The system of claim 10 wherein the at least one muscle group of the patient comprises at least one of glabella, frontalis, and Orbicularis oculi.

16. The system of claim 10 wherein the dynamic index and the static index for the at least one muscle group of the patient is determined using a machine learning algorithm.

17. The system of claim 10 wherein the first computing device and the second computing device are different devices.

18. The system of claim 10 wherein the second computing device is further configured to overlay the patient treatment plan on a digital image of the patient.

\* \* \* \* \*